United States Patent
Ling et al.

(10) Patent No.: US 6,329,499 B1
(45) Date of Patent: *Dec. 11, 2001

(54) METHODS FOR TREATMENT OF MULTIPLE SCLEROSIS USING PEPTIDE ANALOGUES OF HUMAN MYELIN BASIC PROTEIN

(75) Inventors: Nicholas Ling; Amitabh Gaur, both of San Diego; Paul J. Conlon, Solana Beach; Lawrence Steinman, Palo Alto, all of CA (US)

(73) Assignee: Neurocrine Biosciences, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/342,408

(22) Filed: Nov. 18, 1994

(51) Int. Cl.$^7$ ............................ A61K 38/08; A61K 38/10
(52) U.S. Cl. .......................... 530/327; 530/326; 530/328; 530/329; 514/14; 514/15; 514/16; 514/17
(58) Field of Search ........................ 514/14–17; 530/326, 530/327, 328, 329

(56) References Cited

U.S. PATENT DOCUMENTS

| | | | |
|---|---|---|---|
| 5,288,639 | * | 2/1994 | Burnie et al. . |
| 5,559,209 | * | 9/1996 | Nishimoto et al. .................. 530/326 |
| 5,948,764 | * | 9/1999 | Gaur et al. ............................ 514/14 |
| 6,036,957 | | 3/2000 | Weiner et al. .................... 424/184.1 |

FOREIGN PATENT DOCUMENTS

| | | |
|---|---|---|
| 304 279 B1 | 2/1989 | (EP) . |
| 06157591 | * 6/1994 | (JP) . |
| WO 91/12816 | 9/1991 | (WO) . |
| WO 92/21367 | 12/1992 | (WO) . |
| WO 93/08212 | 4/1993 | (WO) . |
| WO 93/21222 | 10/1993 | (WO) . |
| WO 95/08572 | 3/1995 | (WO) . |
| WO 96/12731 | 5/1996 | (WO) . |
| WO 96/16085 | 5/1996 | (WO) . |
| WO 96/16086 | 5/1996 | (WO) . |
| WO 96/28470 | 9/1996 | (WO) . |

OTHER PUBLICATIONS

Bellacosa et al. A retroviral oncogen, akt, encoding a serine–threonine kinase. Science, 254 (5029) 274–7, 1991.*
Pautot et al . Leucine aminopeptidase: Proc. Natl. Acad. Sci., 90 (21) 9906–9910, 1993.*
Carter and Rodriguez, "Immunosuppressive Treatment of Multiple Sclerosis," *Mayo Clin. Proc. 64*: 664–669, 1989.
Kuchroo et al., "A Single TCR Antagonist Peptide Inhibits Experimental Allergic Encephalomyelitis Mediated by a Diverse T Cell Repertoire," *Journal of Immunology* 153:3326–3336, 1994.
Lamont et al., "Inhibition of Experimental Autoimmune Encephalomyelitis Induction In SJL/J Mice By Using A Peptide With High Affinity For IA$^S$ Molecules," *Journal of Immunology* 145(6): 1687–1693, 1990.
Martin et al., "Immunological Aspects of Demyelinating Diseases," *Annu. Rev. Immunol. 10*: 153–87, 1992.
Sakai et al., "Prevention of experimental encephalomyelitis with peptides that block interaction of T cells with major histocompatibility complex proteins," *Proc. Natl. Acad. Sci. USA 86*: 9470–9474, 1989.
Steinman et al., "The Epigenetics Of Multiple Sclerosis: Clues to Etiology and a Ration for Immune Therapy," *Annu. Rev. Neurosci. 17*: 247–65, 1994.
Teitelbaum et al., "Specific inhibition of the T–cell response to myelin basic protein by the synthetic copolymer Cop 1," *Proc. Natl. Acad. Sci. USA 85*: 9724–9728, 1988.
Vogt et al., "Ligand Motifs of HLA–DRB5*0101 and DRB1*1501 Molecules Delineated from Self–Peptides," *Journal of Immunology* 153: 1665–1673, 1994.
Wraith et al., "Antigen Recognition in Autoimmune Encephalomyeltitis and the Potential for Peptide–Mediated Immunotherapy," *Cell 59*: 247–255, 1989.
Wucherpfennig et al., "Structural Requirements for Binding of an Immunodominant Myelin Basic Protein Peptide to DR2 Isotypes and for Its Recognition by Human T Cell Clones," *J. Exp. Med. 179*: 279–290, 1994.
Chou et al., "Identity of Myelin Basic Protein from Multiple Sclerosis and Human Control Brains: Discovery of a Genetic Variant," *Journal of Neurochemistry 30*: 745–750, 1978.
Einstein et al., "Suppression of Experimental Allergic Encephalomyelitis By Chemically Modified Encephalitogen," *Immunochemistry 9*: 1013–1019, 1972.
Evavold and Allen, "Separation of IL–4 Production from Th Cell Proliferation by an Altered T Cell Receptor Ligand," *Science 252*: 1308–1310, 1991.
Gautam et al., "A Polyalanine Peptide With only Five Native Myelin Basic Protein Residues Induces Autoimmune Encephalomyelitis," *J. Exp. Med. 176*: 605–609, 1992.
Hashim et al., "Suppression and Reversal of Allergic Encephalomyelitis in Guinea Pigs with a Non–Encephalitogenic analogue of the Tryptophan Region of the Myelin Basic Protein," *Journal of Immunology 127*(3): 862–866, 1981.

(List continued on next page.)

*Primary Examiner*—Michael Borin
(74) *Attorney, Agent, or Firm*—Seed Intellectual Property Law Group PLL

(57) ABSTRACT

The present invention is directed toward peptide analogues of human myelin basic protein. The peptide analogue is at least seven amino acids long and derived from residues 86 to 99 of human myelin basic protein. The analogues are altered from the native sequence at least at positions 91, 95, or 97. Additional alterations may be made at other positions. Pharmaceutical compositions containing these peptide analogues are provided. The peptide analogues are useful for treating multiple sclerosis.

8 Claims, 4 Drawing Sheets

OTHER PUBLICATIONS

Figure 2:
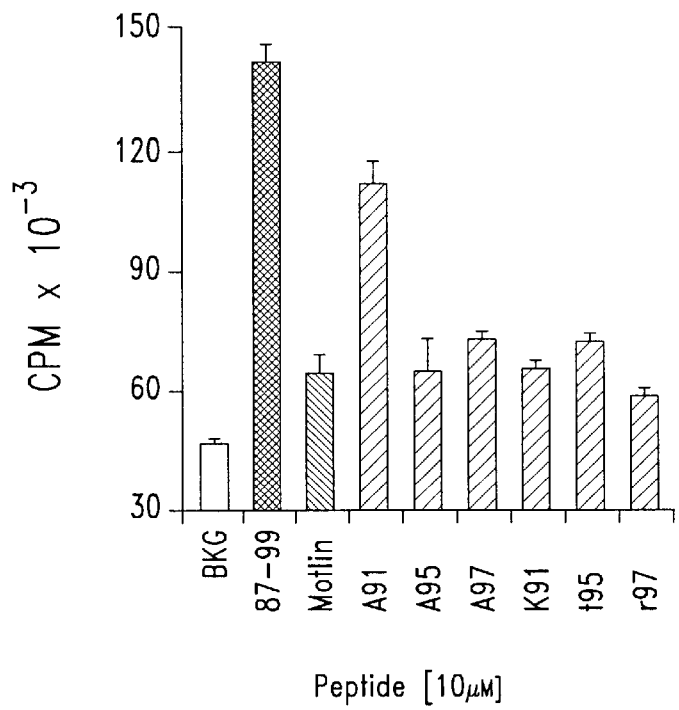

Kardys and Hashim, "Experimental Allergic Encephalomyeltitis in Lewis Rats: Immunoregulation of Disease By a Single Amino Acid Substitution in the Disease–Inducing Determinant," *Journal of Immunology 127*(3): 862–866, 1981.

Karin et al., "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production," *J. Exp. Med. 180*: 2227–2237, 1994.

Martin et al., "Diversity in Fine Specificity and T Cell Receptor Usage of the Human CD4+ Cytotoxic T Cell Response Specific for the Immunodominant Myelin Basic Protein Peptide 87–106," *Journal of Immunology 148* (5): 1359–1366, 1992.

Servis et al., "Two adjacent epitopes on a synthetic dodecapeptide induce lactate dehydrogenase B–specific helper and suppressor T cells," *Proc. R. Soc. Lond. B 228*: 461–470, 1986.

Sette et al., "Analysis of lysozyme–specific immune responses by synthetic peptides. I. Characterization of antibody and T cell–mediated responses to the N–terminal peptide of hen egg–white lysozyme," *Eur. J. Immunol. 16*: 1–6, 1986.

Smilek et al., "A single amino acid change in a myelin basic protein peptide confers the capacity to prevent rather than induce experimental autoimmune encephalomyelitis," *Proc. Natl. Acad. Sci. USA 88*: 9633–9637, 1991.

Su et al., "Synthetic Myelin Basic Protein Peptide Analogs Are Specific Inhibitors of Phospholipid/Calcium–Dependent Protein Kinase (Protein Kinase C)," *Biochemical and Biophysical Research Communications 134*(1): 78–84, 1986.

Abstract 65027 from *Biol. Abstr. 81*(7): AB–701 (1985) of the article "Monoclonal antibodies to human myelin basic protein," *J. Neurochem. 46*(1): 47–53, 1985.

Acha–Orbea et al., "Limited Heterogeneity of T Cell Receptors from Lymphocytes Mediating Autoimmune Encephalomyelitis Allows Specific Immune Intervention," *Cell 54*: 263–273, 1988.

Babbitt et al., "Antigenic competition at the level of peptide–Ia–binding," *Proc. Natl. Acad. Sci. USA 83*: 4509–4513, 1986.

Bernard, "Experimental Autoimmune Encephalomyelitis in Mice: Genetic Control of Susceptibility," *Journal of Immunogenetics 3*: 263–274, 1976.

Brocke et al., "In Vitro Proliferative Responses and Antibody Titers Specific to Human Acetycholine Receptor Synthetic Peptides in Patients with Myasthenia Gravis and Relation to HLA Class II Genes," *J. Clin. Invest. 82*: 1894–1900, 1988.

Brostoff and Howell, "T Cell Receptors, Immunoregulation, and Autoimmunity," *Clinical Immunology and Immunopathology 62*(1): 1–7, 1992.

Day et al., "The Polyclonal Antibody Responses of Lewis Rats to the Synthetic Encephalitogenic Neuropeptide S55S (Residues 72–84 of Guinea Pig Myelin Basic Protein) and Its Analogs," *Journal of Neuroscience Research 18*: 214–221, 1987.

Gammon et al., "Neonatal T–cell tolerance to minimal immunogenic peptides is caused by clonal inactivation," *Nature 319*: 413–415, 1986.

Gaur et al., "Amerlioration of Autoimmune Encephalomyelitis by a Myelin Basic Protein Synthetic Peptide–Induced Anergy," *Science* (258): 1491–1494, 1992.

Gautam et al., "Inhibition Of Experimental Autoimmune Encephalomyelitis By A Nonimmunogenic Non–Self Peptide That Binds To I–A$^{u1}$," *The Journal Of Immunology 148*(10): 3049–3054, 1992.

Hadden et al., "Thymic Hormones, Interleukins, Endotoxin and Thymomimetic Drugs in T Lymphocyte Ontogeny," in *Advances in Immunopharmacology 3*, L. Chedid et al. (Eds.), 1985, pp. 487–497.

Hashim and Day, "Synthetic Peptide Analogs to Probe the Immunological Expression of the Rat Encephalitogenic Neuropeptide," *Journal of Neuroscience Research 18*: 209–213, 1987.

Hashim, "Experimental Allergic Encephalomyelitis: Activation of Suppressor T Lymphocytes by a Modified Sequence of the T Effector Determinant," *Journal of Immunology 126*(2): 419–423, 1981.

Jahnke et al., "Sequence Homology Between Certain Viral Proteins and Proteins Related to Encephalomyelitis and Neuritis," *Science 229*: 282–284, 1985.

Kira et al., "Experimental Allergic Encephalomyelitis in Rabbits. A Major Encephalitogenic Determinant within Residues 1–44 of Myelin Basic Protein," *J. of Neuroimmunol. 12*(3): 183–193, 1986.

Lehninger, "The Amino Acid Building Blocks of Proteins," in *Biochemistry*, 2$^{nd}$ ed., Worth Publishers, Inc. pp. 71–75, 1975.

Martin et al., "A Myelin Basic Protein Peptide is Recognized by Cytotoxic T Cells in the Context of Four HLA–DR Types Associated with Multiple Sclerosis," *Journal of Experimental Medicine 173*: 19–24, 1991.

Rothbard, "Peptides and the Cellular Immune Response," *Ann. Inst. Pasteur/Virologie 137 E*: 518–526, 1986.

Rothbard and Taylor, "A sequence pattern common to T cell epitopes," *EMBO J. 7*(1): 93–100, 1988.

Rudinger, "Characteristics of the amino acids as components of a peptide hormone sequence," in *Peptide Hormones*, J. A. Parsons (ed.), University Park Press, Baltimore, pp. 1–7, 1976.

Sriram et al., "Administration of Myelin Basic Protein–Coupled Spleen Cells Prevents Experimental Allergic Encephalitis," *Cellular Immunology 75*: 378–382, 1983.

Steinman et al., "Regulation of autosensitisation to encephalitogenic myelin basic protein by macrophage–associated and soluble antigen," *Nature 265*: 173–175, 1977.

Steinman et al., "Natural occurrence of thymocytes that react with myelin basic protein," *Neurology 30*(7): 755–759, 1980.

Talmadge et al., "Screening Models for Biological Response Modifiers," in *13$^{th}$International Congress of Chemotherapy. Symposium, Biological Responses Modifiers; SY 64 part 203*, Vienna Aug. 28–Sep. 2, 1993, pp. 203/19–203/34.

Wraith et al., "T Cell Recognition as the Target for Immune Intervention in Autoimmune Disease," *Cell 57*: 709–715, 1989.

Zamvil and Steinman, "The T Lymphocyte in Experimental Allergic Encephalomyellitis," *Annu. Rev. Immunol. 8*: 579–621, 1990.

Zamvil et al., "Encephalitogenic T Cell Clones Specific for Myelin Basic Protein," *J. Exp. Med. 162*: 2107–2124, 1985.

Zamvil et al., "T–cell clones specific for myelin basic protein induce chronic relapsing paralysis and demylination," *Nature 317*: 355–358, 1985.

Zamvil et al., "T–cell epitope of the autoantigen myelin basic protein that induces encephalomyelitis," *Nature 324*: 258–260, 1986.

Zamvil et al., "T–cell Specificity for Class II(I–A) and the Encephalitogenic N–Terminal Epitope of the Autoantigen Myelin Basic Protein," *Journal of Immunology 139*(4): 1075–1079, 1987.

Zamvil et al., "Multiple Discrete Encephalitogenic Epitopes of the Autoantigen Myelin Basic Protein Include a Determinant for I–E Class II Restricted T Cells," *J. Exp. Med. 168*: 1181–1186, 1988.

Arimilli et al., "Identification of Core Structure and Critical T Cell Receptor Contact Residues in an Antigenic Peptide by Measuring Acidification Rates," *Journal of Immunological Methods 212*:49–59, 1998.

Ausubel et al., "Changes in Cytokine Secretion Induced by Altered Peptide Ligands of Myelin Basic Protein Peptide 85–99," *The Journal of Immunology 159*:2502–2512, 1997.

* cited by examiner

ATGGCGTCACAGAAGAGACCCTCCCAGAGGCACGGATCCAAGTACCTGGCCACAGCAAGTACCATGGACC
1
M A S Q K R P S Q R H G S K Y L A T A S T M D

ATGCCAGGCATGGCTTCCTCCCAAGGCACAGAGACACGGGCATCCTTGACTCCATCGGGCGCTTCTTTGG

H A R H G F L P R H R D T G I L D S I G R F F G

CGGTGACAGGGGTGCGCCAAAGCGGGGCTCTGGCAAGGACTCACACCACCCGGCAAGAACTGCTCACTAT

G D R G A P K R G S G K D S H H P A R T A H Y

GGCTCCCTGCCCCAGAAGTCACACGGCCGGACCCAAGATGAAAACCCCGTAGTCCACTTCTTCAAGAACA

G S L P Q K S H G R T Q D E N P V V H F F K N

TTGTGACGCCTCGCACACCACCCCCGTCGCAGGGAAAGGGGAGAGGACTGTCCCTGAGCAGATTTAGCTG

I V T P R T P P P S Q G K G R G L S L S R F S W

GGGGGCCGAAGGCCAGAGACCAGGATTTGGCTACGGAGGCAGAGCGTCCGACTATAAATCGGCTCACAAG

G A E G Q R P G F G Y G G R A S D Y K S A H K

GGATTCAAGGGAGTCGATGCCCAGGGCACGCTTTCCAAAATTTTTAAGCTGGGAGGAAGAGATAGTCGCT

G F K G V D A Q G T L S K I F K L G G R D S R

CTGGATCACCCATGGCTAGACGCTGA

S G S P M A R R

*Fig. 1*

METHODS FOR TREATMENT OF MULTIPLE SCLEROSIS USING PEPTIDE ANALOGUES OF HUMAN MYELIN BASIC PROTEIN

TECHNICAL FIELD

The present invention relates generally to methods for treating multiple sclerosis by using peptide analogues of human myelin basic protein.

BACKGROUND OF THE INVENTION

Multiple sclerosis (MS) is a chronic, inflammatory disease that affects approximately 250,000 individuals in the United States. Although the clinical course may be quite variable, the most common form is manifested by relapsing neurological deficits, in particular, paralysis, sensory deficits, and visual problems.

The inflammatory process occurs primarily within the white matter of the central nervous system and is mediated by T lymphocytes, B lymphocytes, and macrophages. These cells are responsible for the demyelination of axons. The characteristic lesion in MS is called the plaque due to its macroscopic appearance.

Multiple sclerosis is thought to arise from pathogenic T cells that somehow evaded mechanisms establishing self-tolerance, and attack normal tissue. T cell reactivity to myelin basic protein may be a critical component in the development of MS. The pathogenic T cells found in lesions have restricted heterogeneity of antigen receptors (TCR). The T cells isolated from plaques show rearrangement of a restricted number of Vα and Vβ gene segments. In addition, the TCRs display several dominant amino acid motifs in the third complementarity determining region (CDR), which is the major antigen contact site. All together, three CDR3 motifs have been identified in T cell clones known to recognize an epitope within amino acids 86–106 of myelin basic protein. These motifs were found in 44% of rearranged TCR sequences involving one particular Vβ gene rearranged in T cells isolated from brain of two patients with MS.

A definitive treatment for MS has not been established. Historically, corticosteroids and ACTH have been used to treat MS. Basically, these drugs reduce the inflammatory response by toxicity to lymphocytes. Recovery may be hastened from acute exacerbations, but these drugs do not prevent future attacks or prevent development of additional disabilities or chronic progression of MS (Carter and Rodriguez, *Mayo Clinic Proc.* 64:664, 1989; Weiner and Hafler, *Ann. Neurol.* 23:211, 1988). In addition, the substantial side effects of steroid treatments make these drugs undesirable for long-term use.

Other toxic compounds, such as azathioprine, a purine antagonist, cyclophosphamide, and cyclosporine have been used to treat symptoms of MS. Like corticosteroid treatment, these drugs are beneficial at most for a short term and are highly toxic. Side effects include increased malignancies, leukopenias, toxic hepatitis, gastrointestinal problems, hypertension, and nephrotoxicity (Mitchell, *Cont. Clin. Neurol.* 77:231, 1993; Weiner and Hafler, supra). Antibody based therapies directed toward T cells, such as anti-CD4 antibodies, are currently under study for treatment of MS. However, these agents may cause deleterious side effects by immunocompromising the patient.

More recently, cytokines such as IFN-γ and IFN-β have been administered in attempts to alleviate the symptoms of MS. However, a pilot study involving IFN-γ was terminated because 7 of 18 patients treated with this drug experienced a clinical exacerbation within one month after initiation of treatment. Moreover, there was an increase in the specific response to MBP (Weiner and Hafler, supra).

Betaseron, a modified beta interferon, has recently been approved for use in MS patients. Although Betaseron treatment showed some improvement in exacerbation rates (Paty et al., *Neurology* 43:662, 1993), there was no difference in the rate of clinical deterioration between treated and control groups (IFNB MS Study Group, *Neurology* 43:655, 1993; Paty et al., supra). Side effects were commonly observed. The most frequent of such side effects were fever (40%–58% of patients), flu-like symptoms (76% of patients), chills (46% of patients), mylagias (41% of patients), and sweating (23% of patients). In addition, injection site reactions (85%), including inflammation, pain, hypersensitivity and necrosis, were common (IFNB MS Study Group, supra; Connelly, *Annals of Pharm.* 28:610, 1994).

In view of the problems associated with existing treatments of MS, there is a compelling need for improved treatments which are more effective and are not associated with such disadvantages. The present invention exploits the use of peptide analogues which antagonize a T cell response to human myelin basic protein to effectively treat MS, while providing other related advantages.

SUMMARY OF THE INVENTION

The present invention provides peptide analogues comprising at least 7 amino acids selected from residues 86 to 99 of human myelin basic protein (SEQ. ID No:3) in which either L-lysine at position 91, L-threonine at position 95, or L-arginine at position 97 is altered to another amino acid. In one embodiment, L-lysine at position 91 is altered and one to three additional L-amino acids selected from residues 86, 87, 88, 95, 98 or 99 are altered to another amino acid. In a second embodiment, L-threonine at position 95 is altered and one to three additional amino acids selected from residues 86, 87, 88, 91, 98 and 99 or 86, 87, 88, 97, 98, and 99 are altered to another amino acid. In a third related embodiment, L-arginine at position 97 is altered and one to three additional amino acids selected from residues 86, 87, 88, 95, 98 or 99 are altered to another amino acid. The peptide analogues preferably contain double or triple alterations. In preferred aspects of the invention, the peptide analogues have altered residues 91, 95 or 97 to alanine and the additional amino acids are altered to the corresponding D-form amino acid.

In other embodiments, peptide analogues comprise at least seven amino acids selected from residues 86 to 99 of human myelin basic protein (SEQ. ID No:3) in which either L-lysine at position 91, L-threonine at position 95, or L-arginine at position 97 is altered to another amino acid, and in addition the N-terminal and C-terminal amino acids are altered in order to reduce proteolysis upon administration of the peptide analogue. In a preferred aspect, the N-and C-terminal amino acids are of the D-form.

In other embodiments, the peptide analogues comprise at least seven amino acids selected from residues 86 to 99 of human myelin basic protein (SEQ. ID No:3) in which either L-lysine at position 91, L-threonine at position 95, or L-arginine at position 97 is altered to another amino acid and in addition up to three other amino acid alterations are made. Any residue within 86–99 may be altered except that in a peptide analogue in which residue 91 is altered, residue 97 may not be altered. Likewise, in a peptide analogue in which residue 97 is altered, residue 91 may not be altered.

Other embodiments provide peptide analogues comprising at least seven amino acids selected from residues 86 to 99 of human myelin basic protein (SEQ. ID NO:3) in which either L-lysine at position 91, L-threonine at position 95, or L-arginine at position 97 is altered to another amino acid. In preferred aspects, residue 91, 95 or 97 are altered to either alanine or the corresponding D-amino acid.

Further aspects of the present invention provide a pharmaceutical composition comprising a peptide analogue according to the embodiments set out above in which the peptide analogue is contained in a physiologically acceptable carrier or diluent.

Further aspects of the present invention provide methods of treating multiple sclerosis by administering to a patient a therapeutically effective amount of a pharmaceutical composition comprising a peptide analogue comprising at least seven amino acids selected from residues 86 to 99 of human myelin basic protein (SEQ. ID No:3) in which residues 91, 95 or 97 are altered to another amino acid. Additionally, one to three additional amino acids may be altered or the N-and C-ends are altered to reduce proteolysis upon administration.

These and other aspects of the invention will become evident upon reference to the following detailed description and attached drawings. In addition, various references are set forth below which describe in more detail certain procedures or compositions. Each of these references are incorporated herein by reference in their entirety as if each were individually noted for incorporation.

BRIEF DESCRIPTION OF THE DRAWINGS

FIG. 1 depicts DNA and predicted (SEQ ID No:1) (SEQ ID No:2) amino acid sequence for human myelin basic protein.

FIG. 2 depicts the response of draining lymph node cells from Lewis rats immunized 9–10 days previously with MBP (87–99) to 10 μM of MBP (87–99), medium, the unrelated peptide motilin, and six different MBP analogues. A, alanine; k, D-lysine; t, D-threonine; r, D-arginine.

FIG. 3 is a graph displaying the proliferative response of the T cell line NBI to residue 91-substituted analogues of human myelin basic protein (87–99). Ten different substitutions were tested. The proliferative response of the rat T cell line in response to concentrations of peptide analogues ranging from 0 to 150 μM was determined. The extent of proliferation is shown as counts per minute; standard errors of the mean were less than ±10%. MOT, motilin, a peptide unrelated to MBP; MBP (87–99), human myelin basic protein residues 87–99; K, lysine; R, arginine; N, asparagine; H, histidine; L, leucine; S, serine; G, glycine; k, D-Lysine; E, glutamic acid; F, phenylalanine; A, alanine.

FIG. 4 is a graph displaying the proliferative response of the T cell line NBI to residue 95-substituted analogues of human myelin basic protein (87–99). Ten different substitutions were tested. The proliferative response of the rat T cell line in response to concentrations of peptide analogues ranging from 0 to 150 μM was determined. The extent of proliferation is shown as counts per minute; standard errors of the mean were less than ±10%. MOT, motilin, a peptide unrelated to MBP; MBP (87–99), human myelin basic protein residues 87–99; T, threonine; A, alanine; t, D-threonine; G, glycine; I, isoleucine; Y, tyrosine; Q, glutamine; S, serine; K, lysine; E, glutamic acid; H, histidine.

FIG. 5 is a graph displaying the proliferative response of the T cell line NBI to residue 97-substituted analogues of human myelin basic protein. Eleven different substitutions were tested. The proliferative response of the T cells to concentrations of peptide analogues ranging from 0 to 150 μM was determined. The extent of proliferation is displayed as counts per minute. MBP 87–99, myelin basic protein (87–99); R, arginine; a, D-alanine; r, D-arginine; G, glycine; K, lysine; Q, glutamine; E, glutamic acid; T, threonine; L, leucine; F, phenylalanine; H, histidine; A, alanine.

FIG. 6 is a graph illustrating the ability of peptide analogues of MBP to inhibit proliferation of rat T cells that are reactive to MBP. The proliferative response of draining lymph node cells from rats immunized with MBP (87–99) to 16.7, 50, or 150 μM of each analogue, or 5 μM of MBP (87–99) is displayed. Analogues were added in the presence of 5 μM MBP (87–99). The extent of proliferation is shown as counts per minute. Controls consisted of MBP (87–99) only at 5 μM and medium only. h88/A91 refers to a representative peptide analogue of MBP (87–99) with D-histidine at residue 88 and alanine at residue 91; h88/A91/p99 refers to another representative peptide analogue of MBP (87–99) with D-histidine at 88, alanine at residue 91, and D-proline at residue 99.

FIG. 7 is a graph demonstrating the inhibition of EAE induction in Lewis rats following injection of MBP (87–99). Arrows indicate days that either PBS (control) or h88/A91 peptide analogue were administered. EAE was recorded as 0, no symptoms; 1, tail paralysis; 2, hind limb weakness; 3, hind limb paralysis; 4, hind and front limb paralysis.

DETAILED DESCRIPTION OF THE INVENTION

Prior to setting forth the invention, it may be helpful to an understanding thereof to set forth definitions of certain terms that will be used hereinafter. "Human myelin basic protein" ("MBP") refers to a protein found in the cytoplasm of human oligodendroglial cells. The nucleotide sequence and predicted amino acid sequence of human MBP are presented in FIG. 1 (SEQ. ID Nos. 1 and 2.

A. Although not depicted in FIG. 1, different molecular forms of human myelin basic protein generated by differential splicing or post-translational modification are also within the scope of this invention. "Peptide analogues" of myelin basic protein are at least 7 amino acids in length and contain at least one difference in amino acid sequence between the analogue and native human myelin basic protein, one of which is a difference at residue 91, 95 or 97. Unless otherwise indicated, a named amino acid refers to the L-form. An L-amino acid from the native peptide may be altered to any other one of the 20 L-amino acids commonly found in proteins, any one of the corresponding D-amino acids, rare amino acids, such as 4-hydroxyproline, and hydroxylysine, or a non-protein amino acid, such as β-alanine and homoserine. Also included with the scope of the present invention are amino acids which have been altered by chemical means such as methylation (e.g., α-methylvaline), amidation of the C-terminal amino acid by an alkylamine such as ethylamine, ethanolamine, and ethylene diamine, and acylation or methylation of an amino acid side chain function (e.g., acylation of the epsilon amino group of lysine).

"Residue 91,""residue 95, " and "residue 97" (also called position 91, position 95, and position 97, respectively), refer to amino acids 91, 95, and 97 of human myelin basic protein as displayed in FIG. 1 (SEQ ID No:2) or the amino acid at a comparative position. More specifically, the numbering system for these residues relates to the amino acid position within the native human protein, regardless of the length of the peptide or the amino acid position within that peptide.

Peptide Analogues of Myelin Basic Protein

As noted above, the present invention provides peptide analogues comprising at least 7 amino acids selected from residues 86–99 of human myelin basic protein (SEQ. ID No:3) and including an alteration of the naturally occurring L-lysine at position 91, L-threonine at position 95, or L-arginine at position 97, to another amino acid. In one aspect, the peptide analogue includes additional alteration of one to three L-amino acids at positions 86, 87, 88, 91, 95, 97, 98 and/or 99 of human myelin basic protein as long as 91 and 97 are not both altered in the same peptide analogue. In another aspect, the peptide analogue additionally has the N-terminal and C-terminal residues altered to an amino acid such that proteolysis is reduced upon administration to a patient compared to a peptide analogue without these additional alterations. In a further aspect, the peptide analogue of MBP comprises at least seven amino acids selected from residues 86–99 (SEQ. ID No: 3) and has one of the residues at position 91, 95 or 97 altered to an amino acid not present in native MBP protein. In addition to such single alterations, one to three additional alterations of residues 86 to 99 may be made, as long as residues 91 and 97 are not altered in the same peptide analogue.

The peptide analogues are preferably 7 to 16 amino acids, and usually not longer than 20 amino acids. Particularly preferred peptide analogues are 14 amino acids in length. Residues 91, 95, and 97, which are L-lysine, L-threonine, and L-arginine, respectively, in the native human protein, are the key residues. Within the subject invention, analogues must have an amino acid other than L-lysine at position 91, an amino acid other than L-threonine at position 95, or an amino acid other than L-arginine at position 97.

As noted above, any amino acid alteration at position 91 is within the scope of this invention. Preferred peptide analogues include alteration of L-lysine to any one of the following amino acids: D-lysine, alanine, glycine, glutamic acid, phenylalanine, arginine, asparagine, histidine, leucine or serine. These amino acids include both conservative (similar charge, polarity, hydrophobicity, and bulkiness) and non-conservative amino acids. Although typically one might expect that only non-conservative amino acid alterations would provide a therapeutic effect, unexpectedly even conservative changes (e.g., arginine) greatly affect the function of the peptide analogue as compared to the native peptide. Such diversity of substitution is further illustrated by the fact that the preferred amino acids noted above are hydrophobic and hydrophilic, charged and uncharged, polar and non-polar.

In addition, any amino acid substitution at residue 95 is also within the scope of this invention. Preferred peptide analogues contain alterations of L-threonine to any one of the following amino acids: D-threonine, alanine, glycine, isoleucine, tyrosine, glutamine, serine, lysine, glutamic acid and histidine. Other preferred alterations are to non-conservative amino acids. Particularly preferred alterations are to alanine or D-threonine.

Similarly, any amino acid alteration at position 97 is within the scope of this invention. Preferred peptide analogues include alteration of L-arginine to D-alanine, D-arginine, glycine, lysine, glutamine, glutamic acid, threonine, leucine, phenylalanine, histidine or alanine. Other preferred alterations are to non-conservative amino acids. Particularly preferred alterations are to alanine and D-arginine.

In addition, in certain embodiments at least one other amino acid selected from residues 86, 87, 88, 95, 98, or 99 is altered. If two other amino acids are changed, one is preferably selected from residues 86, 87, or 88, and the other is selected from residues 98 or 99. Alternatively, up to three alterations at any positions may be made.

With these general considerations in mind, peptide analogues within the scope of the invention have an alteration of residue 91, residue 95, or of residue 97.

One set of preferred peptide analogues have double alterations. In one embodiment, residue 91 is altered as noted above, residue 87 is altered to D-valine, residue 88 to D-histidine or residue 99 to D-proline. Similarly, in another embodiment, residue 97 is altered as noted above, and either residue 87 is altered to D-valine, residue 88 to D-histidine or residue 99 to D-proline. In yet another embodiment, residue 95 is altered as noted above and residue 87 is altered to D-valine, residue 88 to D-histidine or residue 99 to D-proline.

A second set of preferred peptide analogues have triple substitutions. In one embodiment, residue 91 is altered to alanine, residue 87 is altered to D-valine or residue 88 is altered to D-histidine and residue 99 is altered to D-proline. In another embodiment, residue 97 is altered to alanine, residue 88 is altered to D-histidine and residue 99 to D-proline. In yet another embodiment, residue 95 is altered to alanine, residue 88 is altered to D-histidine and residue 99 to D-proline.

Peptide analogues may be synthesized by standard chemistry techniques, including synthesis by automated procedure. In general, peptide analogues are prepared by solid-phase peptide synthesis methodology which involves coupling each protected amino acid residue to a resin support, preferably a 4-methyl-benzhydrylamine resin, by activation with dicyclohexylcarbodimide to yield a peptide with a C-terminal amide. Alternatively, a chloromethyl resin (Merrifield resin) may be used to yield a peptide with a free carboxylic acid at the C-terminus. Side-chain functional groups are protected as follows: benzyl for serine, threonine, glutamic acid, and aspartic acid; tosyl for histidine and arginine; 2-chlorobenzyloxycarbonyl for lysine and 2,6-dichlorobenzyl for tyrosine. Following coupling, the t-butyloxycarbonyl protecting group on the alpha amino function of the added amino acid is removed by treatment with trifluoroacetic acid followed by neutralization with di-isopropyl-ethylamine. The next protected residue is then coupled onto the free amino group, propagating the peptide chain. After the last residue has been attached, the protected peptide-resin is treated with hydrogen fluoride to cleave the peptide from the resin, as well as deprotect the side chain functional groups. Crude product can be further purified by gel filtration, HPLC, partition chromatography, or ion-exchange chromatography.

Peptide analogues within the present invention should (a) compete for the binding of MBP (87–99) residues 87 to 99 of SEQ. ID NO:2) to MHC; (b) not cause proliferation of an MBP (87–99)-reactive T cell line; and (c) inhibit induction of experimental allergic encephalomyelitis (EAE) by MBP (87–99) in rodents.

Thus, candidate peptide analogues may be screened for their ability to treat MS by (1) an assay measuring competitive binding to MHC, (2) an assay measuring a T cell proliferation, and (3) an assay assessing induction inhibition of EAE.

Those analogues that inhibit binding of the native peptides, do not stimulate proliferation of MBP-reactive cell lines, and inhibit the development of EAE by native human MBP (87–99), are useful therapeutics. Although not essential, a further safety assay may be performed to demonstrate that the analogue does not itself induce EAE.

Binding of peptides to MHC molecules may be assayed on whole cells. Briefly, Lewis rat spleen cells are cultured for 3 hours to allow adherent cells to stick to polystyrene petri dishes. Non-adherent cells are removed. Adherent cells, which contain cells expressing MHC class II molecules, are collected by scraping the dishes. The binding of peptide analogues to cells is measured by a fluorescence assay. In this assay, splenic adherent cells are mixed with different concentrations of peptide analogues and incubated for 1 hour at 37° in a $CO_2$ incubator. Following incubation, biotin-labeled MBP (87–99) is added to the culture wells. The cells are incubated for another hour and then washed three times in medium. Phycoerythrin-conjugated or fluorescein-conjugated streptavidin is added along with a fluorochrome-labeled OX-6 or OX-17 monoclonal antibody, which reacts with rat MHC Class II I-A and I-E, respectively. The cells are washed twice before analysis by flow cytometry. Fluorescence intensity is calculated by subtracting the fluorescence value obtained from cells stained with phycoerythrin-streptavidin alone (control staining) from the fluorescence value obtained from biotin-labeled MBP (87–99) plus phycoerythrin-streptavidin (experimental staining). Staining without analogue establishes a 100% value. Percent inhibition is calculated for each analogue and expressed as $IC_{50}$ values. A peptide analogue with an $IC_{50}$ value of less than 100 μM is suitable for further screenings.

Candidate peptide analogues are further tested for their property of causing or inhibiting proliferation of T cell lines. Two different assays may be used as alternatives. The first measures the ability of the analogue to cause proliferation of T cells in a direct fashion. The second measures the ability of the peptide analogue to inhibit proliferation of T cells induced by native MBP (87–99) peptide.

In the direct proliferation assay, MBP (87–99) reactive T cell lines may be used as target cells. T cell lines are established from lymph nodes taken from rats injected with MBP (87–99). Lymph node cells are isolated and cultured for 5 to 8 days with MBP (87–99) and IL-2 as a source of T cell growth factors. Viable cells are recovered and a second round of stimulation is performed with MBP (87–99) and irradiated splenocytes as a source of growth factors. After 5 to 6 passages in this manner, the proliferative potential of the cell lines are determined. MBP-reactive lines are used in the proliferation assay. In this assay, T cell lines are cultured for three days with various concentrations of peptide analogues and irradiated, autologous splenocytes. After three days, 0.5–1.0 μCi of [$^3$H]-thymidine is added for 12–16 hours. Cultures are harvested and incorporated counts determined. Mean CPM and standard error of the mean are calculated from triplicate cultures.

As an alternative to the use of T cell lines as described above, draining lymph node cells from Lewis rats injected with MBP (87–99) may be used. Preferably, this assay is used in combination with the proliferation assay using T cell lines. Briefly, Lewis rats are injected subcutaneously with MBP (87–99) peptide in complete Freund's adjuvant. Nine to ten days later, draining lymph node cells are isolated and single-cell suspensions are prepared. Lymph node cells are incubated with various concentrations of peptide analogues for three days in a humidified air chamber containing 6.5% $CO_2$. After incubation, the cultures are pulsed with 1–2 μCi of [$^3$H]-thymidine for 12–18 hours. Cultures are harvested on fiberglass filters and counted in a scintillation counter. Mean CPM and the standard error of the mean are calculated from data determined in triplicate cultures. Peptide analogues yielding results that are more than three standard deviations of the mean response with a comparable concentration of MBP (87–99) are considered non-stimulatory. Peptide analogues which do not stimulate proliferation at concentrations of less than or equal to 50 μM are suitable for further screenings.

The second or alternative assay is a competition assay for T cell proliferation. In this assay, antigen presenting spleen cells are first irradiated and then incubated with native MBP (87–99) peptide for 2–4 hours. These cells are then washed and further cultured with T cells reactive to MBP (87–99). Various concentrations of candidate peptide analogues are included in cultures for an additional 3 days. Following this incubation period, each culture is pulsed with 1 μCi of [$^3$H]-thymidine for an additional 12–18 hours. Cultures are then harvested on fiberglass filters and counted as above. Mean CPM and standard error of the mean are calculated from data determined in triplicate cultures. Peptide analogues which inhibit proliferation to approximately 25% at a concentration of 50 μM or greater are suitable for further screening.

Candidate peptides that compete for binding of MBP (87–99) to MHC and do not cause direct proliferation of T cell line or can inhibit proliferation by MBP (87–99), are further tested for their ability to inhibit the induction of EAE by MBP (87–99). Briefly, 500 μg of MBP (87–99) is injected as an emulsion in complete Freund's adjuvant supplemented with heat killed *Mycobacterium tuberculosis* (H37Ra). Rats are injected subcutaneously at the base of the tail with 200 μl of the emulsion. Rats are divided into two groups. Approximately 2 days prior to disease induction (usually 10 days following injection of MBP (87–99)) rats are injected intraperitoneally either with PBS or peptide analogues in PBS. Animals are monitored for clinical signs on a daily basis by an observer blind to the treatment protocol. EAE is scored on a scale of 0–4: 0, clinically normal; 1, flaccid tail paralysis; 2, hind limb weakness; 3, hind limb paralysis; 4, front and hind limbs affected. Peptide analogues injected at 5 mg/kg or less (approximately 1 mg per rat) are considered to inhibit the development of EAE if there is a 50% reduction in the mean cumulative score over seven days following onset of disease symptoms in the control group.

In addition, as a safety measure, but not essential to this invention, suitable peptide analogues may be tested for direct induction of EAE. As described in detail in Example 2, various amounts of peptide analogues are injected at the base of the tail of rats, and the rats examined daily for signs of EAE. A peptide analogue which is not considered to cause EAE has a mean cumulative score of less than or equal to 1 over seven days when 1 mg (5 mg/kg) in complete Freund's adjuvant is injected.

Treatment and Prevention of Multiple Sclerosis

As noted above, the present invention provides methods for treating and preventing multiple sclerosis by administering to the patient a therapeutically effective amount of a peptide analogue of human myelin basic protein as described herein. Patients suitable for such treatment may be identified by criteria establishing a diagnosis of clinically definite MS as defined by the workshop on the diagnosis of MS (Poser et al., *Ann. Neurol.* 13:227, 1983). Briefly, an individual with clinically definite MS has had two attacks and clinical evidence of either two lesions or clinical evidence of one lesion and paraclinical evidence of another, separate lesion. Definite MS may also be diagnosed by evidence of two attacks and oligoclonal bands of IgG in cerebrospinal fluid or by combination of an attack, clinical evidence of two lesions and oligoclonal band of IgG in cerebrospinal fluid. Slightly lower criteria are used for a diagnosis of clinically probable MS.

Effective treatment of multiple sclerosis may be examined in several different ways. Satisfying any of the following criteria evidences effective treatment. Three main criteria are used: EDSS (extended disability status scale), appearance of exacerbations or MRI (magnetic resonance imaging).

The EDSS is a means to grade clinical impairment due to MS (Kurtzke, *Neurology* 33:1444, 1983). Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to MS). A decrease of one full step defines an effective treatment in the context of the present invention (Kurtzke, *Ann. Neurol.* 36:573–79, 1994).

Exacerbations are defined as the appearance of a new symptom that is attributable to MS and accompanied by an appropriate new neurologic abnormality (IFNB MS Study Group, supra). In addition, the exacerbation must last at least 24 hours and be preceded by stability or improvement for at least 30 days. Briefly, patients are given a standard neurological examination by clinicians. Exacerbations are either mild, moderate, or severe according to changes in a Neurological Rating Scale (Sipe et al., *Neurology* 34:1368, 1984). An annual exacerbation rate and proportion of exacerbation-free patients are determined. Therapy is deemed to be effective if there is a statistically significant difference in the rate or proportion of exacerbation-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group.

MRI can be used to measure active lesions using gadolinium-DTPA-enhanced imaging (McDonald et al. *Ann. Neurol.* 36:14, 1994) or the location and extent of lesions using $T_2$-weighted techniques. Briefly, baseline MRIs are obtained. The same imaging plane and patient position are used for each subsequent study. Positioning and imaging sequences are chosen to maximize lesion detection and facilitate lesion tracing. The same positioning and imaging sequences are used on subsequent studies. The presence, location and extent of MS lesions are determined by radiologists. Areas of lesions are outlined and summed slice by slice for total lesion area. Three analyses may be done: evidence of new lesions, rate of appearance of active lesions, percentage change in lesion area (Paty et al., *Neurology* 43:665, 1993). Improvement due to therapy is established when there is a statistically significant improvement in an individual patient compared to baseline or in a treated group versus a placebo group.

Candidate patients for prevention may be identified by the presence of genetic factors. For example, a majority of MS patients have HLA-type DR2a and DR2b. The MS patients having genetic dispositions to MS who are suitable for treatment fall within two groups. First are patients with early disease of the relapsing remitting type. Entry criteria would include disease duration of more than one year, EDSS score of 1.0 to 3.5, exacerbation rate of more than 0.5 per year, and free of clinical exacerbations for 2 months prior to study. The second group would include people with disease progression greater than 1.0 EDSS unit/year over the past two years.

Efficacy of the peptide analogue in the context of prevention is judged based on the following criteria: frequency of MBP reactive T cells determined by limiting dilution, proliferation response of MBP reactive T cell lines and clones, cytokine profiles of T cell lines and clones to MBP established from patients. Efficacy is established by decrease in frequency of reactive cells, a reduction in thymidine incorporation with altered peptide compared to native, and a reduction in TNF and IFN-$\alpha$. Clinical measurements include the relapse rate in one and two year intervals, and a change in EDSS, including time to progression from baseline of 1.0 unit on the EDSS which persists for six months. On a Kaplan-Meier curve, a delay in sustained progression of disability shows efficacy. Other criteria include a change in area and volume of T2 images on MRI, and the number and volume of lesions determined by gadolinium enhanced images.

Peptide analogues of the present invention may be administered either alone, or as a pharmaceutical composition. Briefly, pharmaceutical compositions of the present invention may comprise one or more of the peptide analogues described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients, such as, for example, cytokines like $\beta$-interferon.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulized as a lyophilizate, utilizing appropriate excipients which provide stability as a lyophilizate, and subsequent to rehydration.

Pharmaceutical compositions of the present invention may be administered in a manner appropriate to the disease to be treated (or prevented). The quantity and frequency of administration will be determined by such factors as the condition of the patient, and the type and severity of the patient's disease. Within particularly preferred embodiments of the invention, the peptide analogue or pharmaceutical compositions described herein may be administered at a dosage ranging from 5 to 50 mg/kg, although appropriate dosages may be determined by clinical trials. Patients may be monitored for therapeutic effectiveness by MRI, EDSS, and signs of clinical exacerbation, as described above.

The following examples are offered by way of illustration and not by way of limitation.

EXAMPLE 1

Preparation of Peptides

The peptides were synthesized by solid phase methodology on a peptide synthesizer (Beckman model 990). Peptides with an amidated carboxyl-terminus were prepared with a p-methylbenzhydrylamine resin (MBHA resin); for peptides with a free carboxyl-terminus, a Merrifield resin coupled with the appropriately protected amino acid was used. Both resins were obtained from Bachem Fine Chemicals (Torrance, CA). Derivatized amino acids (Bachem Fine Chemicals) used in the synthesis were of the L-configuration unless specified otherwise, and the N-alpha-amino function protected exclusively with the t-butyloxycarbonyl group. Side-chain functional groups were protected as follows: benzyl for serine, threonine, glutamic acid, and aspartic acid; tosyl for histidine and arginine; 2-chlorobenzyloxycarbonyl for lysine and 2,6-dichlorobenzyl for tyrosine. Coupling of the carboxyl-terminal amino acid to the MBHA resin was carried out with dicyclohexylcarbodiimide and the subsequent amino acids were coupled with dicyclohexylcarbodiimide according to Ling et al. (Proc. *Natl. Acad. Sci. USA* 81:4302, 1984). After the last amino acid was incorporated, the t-butyoxycarbonyl protecting group was removed and the peptide-resin conjugate treated with a mixture of 14 ml hydrofluoric acid (HF), 1.4 ml anisole, and 0.28 ml methylethyl sulfide per gram of resin conjugate at -20° C. for 0.5 hr and at 0° C. for 0.5 hr. HF was removed in vacuum at 0° C., and the resulting peptide and resin mixture was washed twice with diethyl ether and twice with chloroform and diethyl ether alternately. The peptide was extracted five times with 2 M acetic acid, and the extract lyophilized. The lyophilized product was first purified on a column of Sephadex G-25 fine (Pharmacia-LKB, Piscataway, N.J.) developed in 30% acetic acid to remove the truncated fragments and inorganic salts (Ling et al., 1984). Next, peptides were further purified by CM-32 carboxymethylcellulose cation-exchange chromatography (Ling et al., 1984). Final purification was achieved by partition chromatography on Sephadex G-25 fine (Ling et al., 1984). The synthetic product was characterized by amino acid analysis, mass spectrometric analysis, and reversed-phase HPLC.

EXAMPLE 2

Immunizations and EAE Induction

MBP peptide and peptide analogues were dissolved in phosphate-buffered saline (PBS) and emulsified with an equal volume of incomplete Freund's adjuvant supplemented with 4 mg/ml heat-killed *Mycobacterium tuberculosis* H37Ra in oil (Difco Laboratories, Inc., Detroit, Mich.). Rats were immunized subcutaneously at the base of the tail with 0.2 ml containing 500 µg of peptide in the emulsion and were monitored for clinical signs daily. EAE was scored on a scale of 0–4, as follows: 0, clinically normal; 1, flaccid tail; 2, hind limb weakness; 3, hind limb paralysis; 4, front and hind limbs affected.

EXAMPLE 3

Long-Term T Cell Lines

Antigen specific long-term T cell lines were derived using the method developed by Ben-Nun et al. (*Eur. J. Immunol.* 11:195, 1981). Lewis rats were injected with MBP (87–99) as described above. Nine to ten days later draining lymph node cells were cultured ($10^7$/ml) for 5–8 days in stimulation medium together with 10–20 µM of the MBP (87–99) peptide and 15 µl IL-2. After 5 to 8 days of culture, viable cells were collected after Ficoll-Hypaque separation and washed three times. These cells were recultured at $1 \times 10^7$ cells/ml in medium with $5 \times 10^5$ irradiated (3000 rad) autologous splenocytes as accessory cells and 10–20 µM of MBP (87–99). After 5 to 6 stimulation cycles, plates were screened by the ability of cells to proliferate in response to MBP (87–99). Positive lines were transferred to 24-well flat bottom plates and restimulated.

EXAMPLE 4

MHC Binding Assay

The ability of MBP peptides and peptide analogues to bind MHC was measured. An assay which characterizes the binding of peptides to MHC molecules on antigen presenting cells (APC) was employed (Mozes et al., *EMBO J.* 8:4049, 1989; Gautam et al., *PNAS* 91:767, 1994). Spleen cells were cultured in Dulbecco's modified Eagle's medium supplemented with 10% fetal bovine serum (Hyclone Laboratories, Logan, Utah) in standard polystyrene petri dishes (100×15 mm) in a 37° C. incubator containing 6.5% $CO_2$ for 3 hours. Thereafter, non-adherent cells were removed, and the plates were washed three times with PBS. Adherent cells were collected using a cell scraper. The binding of MBP (87–99) analogues was measured using a fluorescence assay. Briefly, $5 \times 10^5$ splenic adherent cells in staining buffer (PBS containing 0.1% bovine serum albumin) were mixed with different concentrations ranging from 0–400 µM of MBP (87–99) analogues in individual wells of U-shape 96-well microculture plates and incubated for 1 hr at 37° C. in a 6.5% $CO_2$ incubator. Following incubation, 10 µM of biotin-labeled MBP (87–99) was added to culture wells for 1 h. Cells were washed three times with the staining buffer. Phycoerythrin-conjugated or fluoroscein-conjugated streptavidin (Becton Dickinson, San Jose, Calif.) was added as a second step reagent (1 µg/well) along with 1 µg/well of fluorochrome-labeled OX-6 or OX-17 monoclonal antibody (Pharmingen, San Diego, Calif.), which reacts with rat MHC class II I-A or I-E, respectively. The cells were washed twice before cytofluorographic analysis on a FACScan (Becton Dickinson). Fluorescence intensity for each sample was calculated by subtracting the fluorescence obtained from OX positive cells stained with phycoerythrin-streptavidin alone (control staining) from the fluorescence obtained from OX positive cells stained with biotin-labeled MBP (87–99) plus phycoerythrin-streptavidin. Percent inhibition was calculated for each analogue and expressed as $IC_{50}$ values.

The peptide analogue, h88/A91, which contains D-histidine at position 88 and alanine at position 91 competed as effectively as MBP (87–99) for MHC against MBP (87–99). At 200 µM, MBP (87–99) inhibited binding by 68.4% and h88/A91 inhibited binding by 67.64%.

EXAMPLE 5

Antigen-specific Lymph Node Cell Proliferation Assay

Female Lewis rates, approximately six weeks old, were purchased from Harlan Sprague, Indianapolis, Ind. MBP peptides were dissolved in phosphate-buffered saline (PBS) and emulsified with an equal volume of complete Freund's adjuvant (Difco Laboratories, Inc., Detroit, Mich.) supplemented with 2 mg/ml of heat-killed *Myobacterium tuberculosis* H37Ra in oil (Difco). Rats were immunized subcutaneously in the base of the tail with 0.1 ml containing 100 µg of the peptide in the emulsion. Nine to ten days following immunization, rats were sacrificed, their draining lymph node removed and a single cell suspension made. Cells were resuspended to $5 \times 10^6$ cells per ml in stimulation medium containing Dulbecco's modified Eagle's medium (Gibco BRL, Gaithersburg, Md.) supplemented with 2 mercaptoethanol ($5 \times 10^5$ M), L-glutamine (2 mM), sodium pyruvate (1 mM), penicillin (100 µg/ml), streptomycin (100 µg/ml), and 1% normal rat serum.

For the assay, 100 µl of the lymph node cell suspension was added to 96-well flat-bottom wells in the presence of an equal volume of medium containing 10 µM of various peptides (including: motilin as a negative control; MBP87–99; medium only or alanine or D-amino acid substituted at position 91, 95, or 97). Cultures were then incubated at 37° C. in humidified air containing 7.5% $CO_2$. After 3 days of incubation, 1.0 µCi of tritiated thymidine (20 Ci/mM; New England Nuclear) was added to each well and the plates reincubated for an additional 12–16 hours. The plates were then harvested with a Matrix filtermate harvester (Packard) and counted using an Automatic Direct Beta Counter (Packard). Mean cpm and the standard error of the mean were calculated from triplicate wells.

As seen in FIG. 2, MBP (87–99) stimulated lymph node cells in contrast to the peptide analogues. Alanine alterations at positions 95 and 97 and D-amino acid alterations at residues 91, 95, and 97 failed to stimulate cells above the control peptide, motilin.

EXAMPLE 6

Antigen-specific T Cell Line Proliferation Assays

Assays for the antigen-specific proliferation assay of T cell lines were performed in 96-well flat bottom microtiter plates as described (Zamvil et al., 1985; Offner et al., 1992; Gold et al., 1992). T cell lines were established as described in Example 3. An initial 1:10 dilution of a 1.5 mM stock solution of MBP or the peptide analogues were added into tissue culture medium. The samples were diluted by three-fold serial dilutions (final volume 100 μl). The responding continuous T cell lines were resuspended to 4×10⁵ cells per ml and 50 μl aliquots added to each well (5×10⁴ cells per well). Approximately 1×10⁶ irradiated (3000R) splenocyte feeder cells were also added to each well. Cultures were then incubated at 37° C. in humidified air containing 7.5% $CO_2$ for 3 days. Twelve to sixteen hours prior to harvesting, 0.5–1.0 μCi of [³H]-thymidine (20 Ci/mM; New England Nuclear) was added to each well and the cultures reincubated. Plates were then harvested with a Matrix filtermate harvester (Packard) and counted using an Automatic Direct Beta Counter (Packard). Mean cpm and the standard error of the mean were calculated from triplicate wells.

Figure 3:
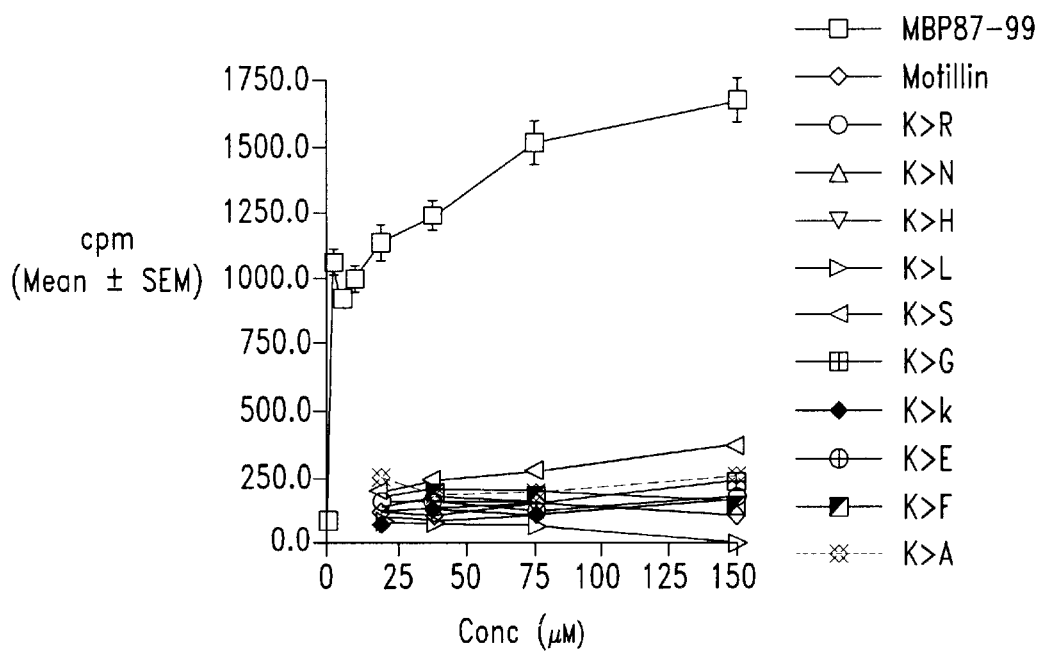
Figure 4:
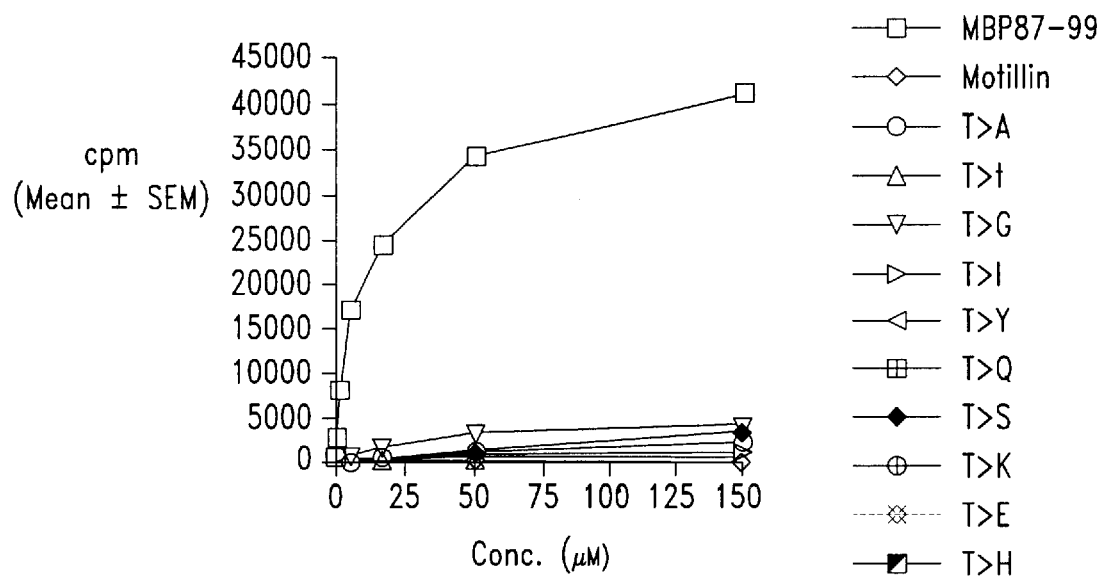
Figure 5:
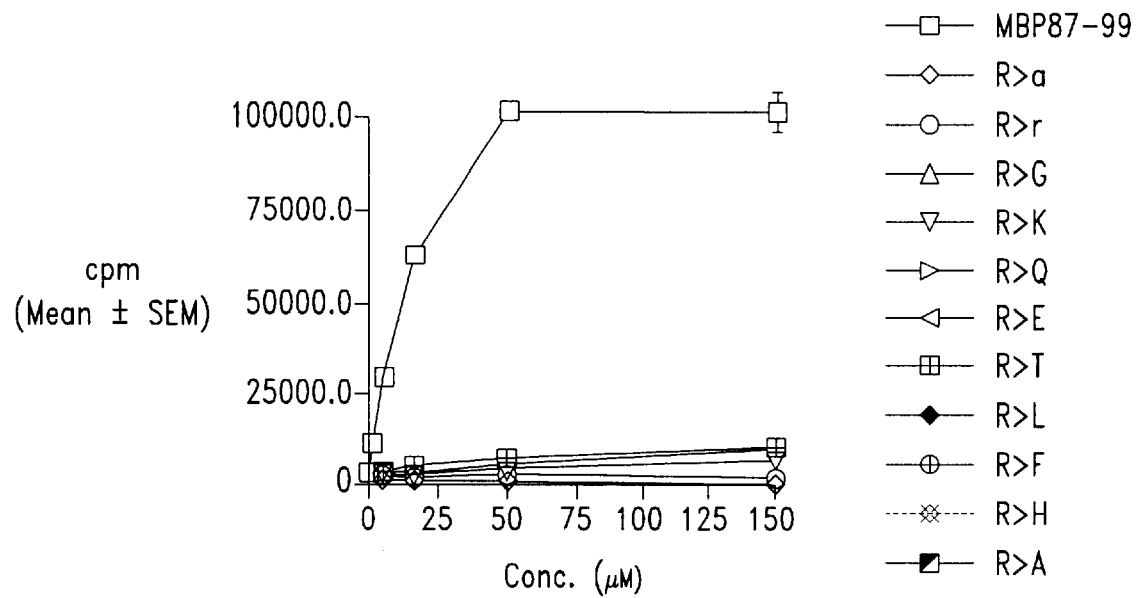

As can be seen in FIGS. 3, 4, and 5 a peptide analogue with any substitution of position 91, 95, or 97 failed to stimulate proliferation of a MBP (87–99)-reactive T cell line. The effect was dramatic as even 150 μM of peptide analogue was 1 to 2 logs less effective at causing proliferation.

EXAMPLE 7

Antagonism of T Cell Proliferation Assay

T cell antagonism was detected in a prepulsed proliferation assay as described by De Magistris et al. (Cell 58:625, 1992) with minor modifications. Antigen presenting spleen cells were γ-irradiated (3000 rad) and incubated with shaking at a concentration of 10⁷ cells/well with 0.2–2.0 μM of the native peptide MBP (87–99) in stimulation medium in 10 ml tissue culture plates for 2.5 hours at 37° C. in humidified air containing 6.5% $CO_2$. Spleen cells were then washed and re-cultured at a concentration of 5×10⁵ cells/well in U-shape 96-well microculture plates together with 5×10⁴ resting MBP (87–99) reactive T cells. Various concentrations of antagonist peptides, ranging from 5–150 μM, were added for an additional 72 hours. Each well was pulsed with 0.5–1 μCi of [³H]-thymidine (specific activity 10 Ci/mmol) for the final 12–16 hours. The cultures were then harvested on fiberglass filters and the proliferative response expressed as CPM±SEM.

Figure 6:
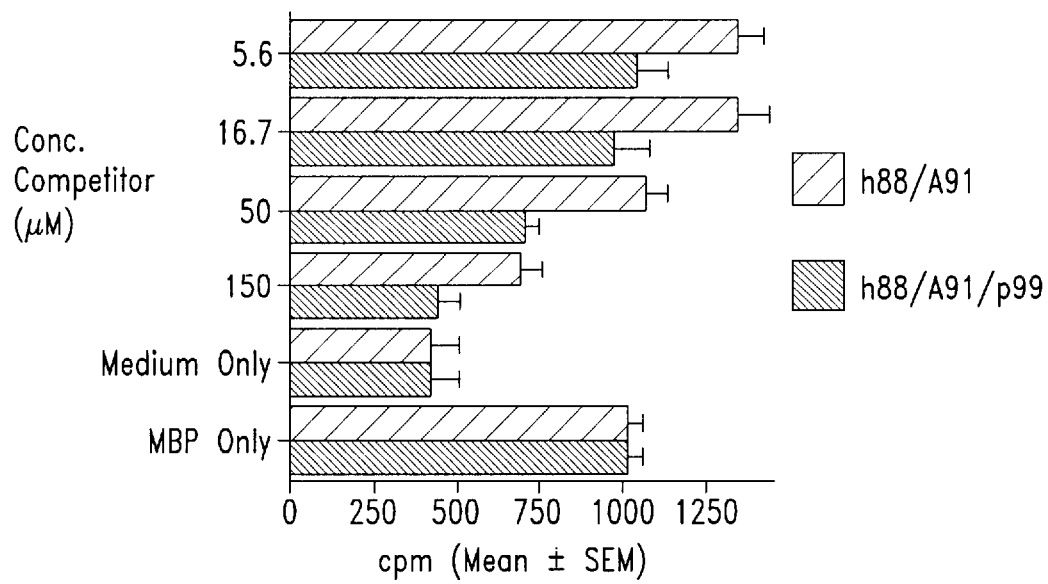

The data presented in FIG. 6 demonstrates that the double altered peptide analogue, h88/A91, and the triple altered peptide analogue, h88/A91/p99, significantly inhibited proliferation of a MBP reactive T cell line. The triple altered analogue caused inhibition at 50 μM and higher concentration, while the double altered analogue caused inhibition at 150 μM.

EXAMPLE 8

Treatment of 87–99 Induced EAE in Lewis Rats

Female Lewis rats, which were 6–8 weeks old, were injected with 500 μg of MBP (87–99) in CFA containing 500 μg of *Mycobacterium tuberculosis* at the base of the tail in 200 μl volume. Rats were divided in groups of 5. The control group received 0.5 ml of PBS and the treatment group received the h88/A91 peptide analogue (1 mg/0.5 ml PBS) intraperitoneally, twice, on days 9 and 10 after immunization. Animals were monitored for disease symptoms on a daily basis. EAE was recorded on the following scale: 0, no symptoms; 1, tail paralysis; 2, hind limb weakness; 3, hind limb paralysis; 4, hind and front limbs affected.

Figure 7:
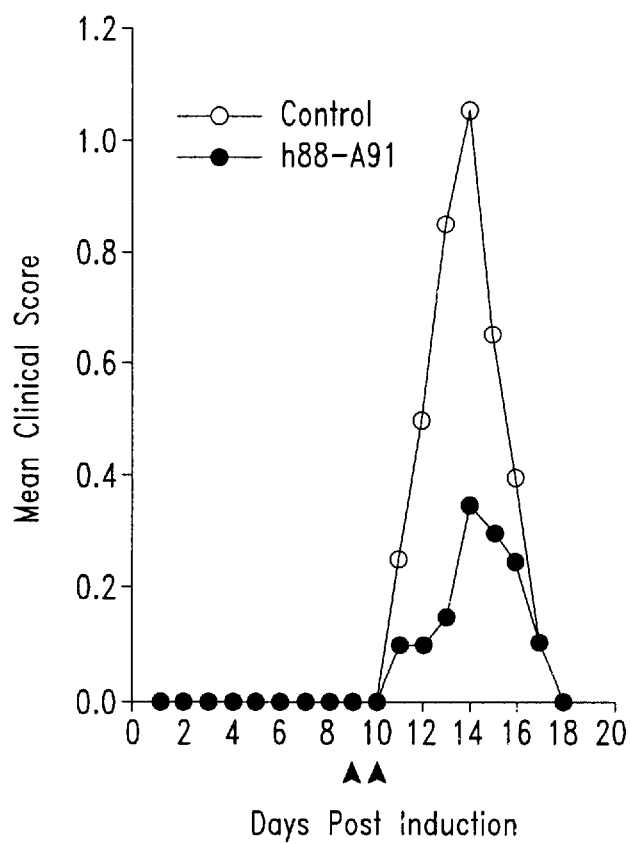

Data from two different experiments was obtained as mean cumulative score of 5 animals (FIG. 7). Untreated control animals went on to develop high level of disease whereas h88/A91 analogue of the MBP peptide 87–99 was effective in preventing significantly the development of EAE in two experiments. Though the analogue was given just before the onset of overt symptoms, it was able to arrest the development of EAE.

EXAMPLE 9

Induction of EAE by Peptide Analogue

The ability of peptide analogues to cause EAE is assessed in vivo. Rats were injected with MBP (87–99) or h88/A91 peptide analogue as described in Example 2. Animals were monitored daily for evidence of EAE. Rats receiving MBP (87–99) had 100% incidence (18/18 rats) of EAE with a mean maximum clinical score of 2.4±0.2. In contrast, 0/12 rats receiving the peptide analogue h88/A91 had EAE. Therefore, this peptide analogue does not induce EAE.

From the foregoing, it will be evident that although specific embodiments of the invention have been described herein for the purpose of illustrating the invention, various modifications may be made without deviating from the spirit and scope of the invention.

---

What is claimed is:

1. A peptide analogue comprising at least seven consecutive amino acids selected from residues 86 to 99 of human myelin basic protein as recited in SEQ ID NO:3, including residue 91, wherein the L-lysine at position 91 is altered to alanine, and proline at position 99 is altered to D-proline.

2. A peptide analogue comprising at least seven consecutive amino acids selected from residues 86 to 99 of human myelin basic protein as recited in SEQ ID NO:3, including residue 91, wherein the L-lysine at position 91 is altered to alanine, and histidine at position 88 is altered to D-histidine and proline at position 99 is altered to D-proline.

3. A peptide analogue comprising at least seven consecutive amino acids selected from residues 86 to 99 of human myelin basic protein as recited in SEQ ID NO:3, including residue 97, wherein the L-arginine at position 97 is altered to alanine, histidine at position 88 is altered to D-histidine, and proline at position 99 is altered to D-proline.

4. A peptide analogue comprising at least seven consecutive amino acids selected from residues 86 to 99 of human myelin basic protein as recited in SEQ ID NO:3, including residue 97, wherein the L-threonine at position 97 is altered to alanine, histidine at position 88 is altered to D-histidine, and proline at position 99 is altered to D-proline.

5. A peptide analogue comprising at least seven consecutive amino acids selected from residues 86 to 99 of human myelin basic protein as recited in SEQ ID NO:3, including residue 95, wherein the L-threonine at position 95 is altered to alanine, and proline at position 99 is altered to D-proline.

6. A peptide analogue comprising at least seven consecutive amino acids selected from residues 86 to 99 of human myelin basic protein as recited in SEQ ID NO:3, including residue 95, wherein the L-threonine at position 95 is altered to alanine, histidine at position 88 is altered to D-histidine and proline at position 99 is altered to D-proline.

7. A peptide analogue comprising at least seven consecutive and unaltered amino acids selected from residues 86 to 99 of human myelin basic protein as recited in SEQ ID NO:3, further comprising residue 91, wherein the L-lysine at position 91 is altered to an amino acid selected from the group consisting of arginine, asparagines, histidine, leucine, serine, glycine, glutamic acid, phenylalanine, alanine, and D-lysine, and the N-terminal amino acid and/or the C-terminal amino acid are altered to another amino acid, such that upon administration of the peptide analogue in vivo proteolysis is reduced.

8. A peptide analogue comprising at least seven consecutive and unaltered amino acids selected from residues 86 to 99 of human myelin basic protein as recited in SEQ ID NO:3, further comprising residue 95, wherein the L-threonine at position 95 is altered to an amino acid selected from the group consisting of alanine, D-threonine, glycine, isoleucine, tyrosine, lysine, glutamic acid, and histidine, and the N-terminal amino acid and/or the C-terminal amino acid are altered to another amino acid, such that upon administration of the peptide analogue in vivo proteolysis is reduced.

* * * * *

UNITED STATES PATENT AND TRADEMARK OFFICE
CERTIFICATE OF CORRECTION

PATENT NO. : 6,329,499 B1
DATED : December 11, 2001
INVENTOR(S) : Nicholas Ling et al.

It is certified that error appears in the above-identified patent and that said Letters Patent is hereby corrected as shown below:

Column 17,
Line 40, "histidine at position 88 is altered to D histidine," should be deleted.
Line 45, "wherein the L-threonine" should read as -- wherein the L-arginine --.

Column 18,
Line 29, "A peptide analogue" should read as -- An analogue to a fragment of human myelin basic protein --.
Line 32, "further comprising residue 91," should be deleted.
Lines 32 and 33, "at position" should read as -- corresponding to position --.
Line 36, -- wherein -- should appear after "and D-lysine, and"
Line 40, "A peptide analogue" should read as -- An analogue to a fragment of human myelin basic protein --.
Line 43, "further comprising residue 95," should be deleted.
Line 44, "at position" should read as -- corresponding to position --.
Line 47, -- wherein -- should appear after "and histidine, and".

Signed and Sealed this

Second Day of March, 2004

JON W. DUDAS
*Acting Director of the United States Patent and Trademark Office*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 513 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..510

(xi) SEQUENCE DESCRIPTION: SEQ ID NO:1:

GCG TCA CAG AAG AGA CCC TCC CAG AGG CAC GGA TCC AAG TAC CTG GCC    48

```
Ala Ser Gln Lys Arg Pro Ser Gln Arg His Gly Ser Lys Tyr Leu Ala
 1               5                  10                  15

ACA GCA AGT ACC ATG GAC CAT GCC AGG CAT GGC TTC CTC CCA AGG CAC     96
Thr Ala Ser Thr Met Asp His Ala Arg His Gly Phe Leu Pro Arg His
             20                  25                  30

AGA GAC ACG GGC ATC CTT GAC TCC ATC GGG CGC TTC TTT GGC GGT GAC    144
Arg Asp Thr Gly Ile Leu Asp Ser Ile Gly Arg Phe Phe Gly Gly Asp
         35                  40                  45

AGG GGT GCG CCA AAG CGG GGC TCT GGC AAG GAC TCA CAC CAC CCG GCA    192
Arg Gly Ala Pro Lys Arg Gly Ser Gly Lys Asp Ser His His Pro Ala
     50                  55                  60

AGA ACT GCT CAC TAT GGC TCC CTG CCC CAG AAG TCA CAC GGC CGG ACC    240
Arg Thr Ala His Tyr Gly Ser Leu Pro Gln Lys Ser His Gly Arg Thr
 65                  70                  75                  80

CAA GAT GAA AAC CCC GTA GTC CAC TTC TTC AAG AAC ATT GTG ACG CCT    288
Gln Asp Glu Asn Pro Val Val His Phe Phe Lys Asn Ile Val Thr Pro
                 85                  90                  95

CGC ACA CCA CCC CCG TCG CAG GGA AAG GGG AGA GGA CTG TCC CTG AGC    336
Arg Thr Pro Pro Pro Ser Gln Gly Lys Gly Arg Gly Leu Ser Leu Ser
             100                 105                 110

AGA TTT AGC TGG GGG GCC GAA GGC CAG AGA CCA GGA TTT GGC TAC GGA    384
Arg Phe Ser Trp Gly Ala Glu Gly Gln Arg Pro Gly Phe Gly Tyr Gly
         115                 120                 125

GGC AGA GCG TCC GAC TAT AAA TCG GCT CAC AAG GGA TTC AAG GGA GTC    432
Gly Arg Ala Ser Asp Tyr Lys Ser Ala His Lys Gly Phe Lys Gly Val
     130                 135                 140

GAT GCC CAG GGC ACG CTT TCC AAA ATT TTT AAG CTG GGA GGA AGA GAT    480
Asp Ala Gln Gly Thr Leu Ser Lys Ile Phe Lys Leu Gly Gly Arg Asp
145                 150                 155                 160

AGT CGC TCT GGA TCA CCC ATG GCT AGA CGC TGA                        513
Ser Arg Ser Gly Ser Pro Met Ala Arg Arg
                 165                 170

(2) INFORMATION FOR SEQ ID NO:2:

(i) SEQUENCE CHARACTERISTICS:
        (A) LENGTH: 170 amino acids
        (B) TYPE: amino acid
        (D) TOPOLOGY: linear (ii) MOLECULE TYPE: protein (xi) SEQUENCE DESCRIPTION: SEQ ID NO:2:

Ala Ser Gln Lys Arg Pro Ser Gln Arg His Gly Ser Lys Tyr Leu Ala
 1               5                  10                  15

Thr Ala Ser Thr Met Asp His Ala Arg His Gly Phe Leu Pro Arg His
             20                  25                  30

Arg Asp Thr Gly Ile Leu Asp Ser Ile Gly Arg Phe Phe Gly Gly Asp
         35                  40                  45

Arg Gly Ala Pro Lys Arg Gly Ser Gly Lys Asp Ser His His Pro Ala
     50                  55                  60

Arg Thr Ala His Tyr Gly Ser Leu Pro Gln Lys Ser His Gly Arg Thr
 65                  70                  75                  80

Gln Asp Glu Asn Pro Val Val His Phe Phe Lys Asn Ile Val Thr Pro
                 85                  90                  95

Arg Thr Pro Pro Pro Ser Gln Gly Lys Gly Arg Gly Leu Ser Leu Ser
             100                 105                 110

Arg Phe Ser Trp Gly Ala Glu Gly Gln Arg Pro Gly Phe Gly Tyr Gly
         115                 120                 125
```

```
Gly Arg Ala Ser Asp Tyr Lys Ser Ala His Lys Gly Phe Lys Gly Val
    130                 135                 140

Asp Ala Gln Gly Thr Leu Ser Lys Ile Phe Lys Leu Gly Gly Arg Asp
145                 150                 155                 160

Ser Arg Ser Gly Ser Pro Met Ala Arg Arg
                165                 170

(2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:3:

Val Val His Phe Phe Lys Asn Ile Val Thr Pro Arg Thr Pro
1               5                   10
```